United States Patent
Chan

(10) Patent No.: US 10,053,269 B2
(45) Date of Patent: Aug. 21, 2018

(54) MULTI-FUNCTIONAL FIBER OPTIC FUEL SENSOR SYSTEM HAVING A PHOTONIC MEMBRANE

(71) Applicant: The Boeing Company, Chicago, IL (US)

(72) Inventor: Eric Yuen-Jun Chan, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 423 days.

(21) Appl. No.: 14/616,793

(22) Filed: Feb. 9, 2015

(65) Prior Publication Data

US 2016/0231231 A1 Aug. 11, 2016

(51) Int. Cl.
| | | |
|---|---|---|
| *G01N 21/00* | (2006.01) | |
| *B65D 65/38* | (2006.01) | |
| *B64D 37/04* | (2006.01) | |
| *B64D 37/00* | (2006.01) | |
| *G01L 9/00* | (2006.01) | |

(Continued)

(52) U.S. Cl.
CPC ........... *B65D 65/38* (2013.01); *B64D 37/005* (2013.01); *B64D 37/04* (2013.01); *G01F 23/164* (2013.01); *G01K 1/00* (2013.01); *G01K 11/32* (2013.01); *G01L 9/0079* (2013.01); *G01N 9/00* (2013.01); *G01N 33/00* (2013.01); *G01N 21/65* (2013.01)

(58) Field of Classification Search
CPC ..... B64D 37/02; G01F 23/164; G01L 9/0079; G01N 21/65
See application file for complete search history.

(56) References Cited

U.S. PATENT DOCUMENTS

| | | |
|---|---|---|
| 4,994,682 A | 2/1991 | Woodside |
| 5,026,984 A | 6/1991 | Gerdt |

(Continued)

FOREIGN PATENT DOCUMENTS

EM 1189039 A1 3/2002

OTHER PUBLICATIONS

Qingxu Yu et al., "Pressure sensor based on the fiber-optic extrinsic Fabry-Perot interferometer," Photonic Sensors, vol. 1, No. 1, Nov. 22, 2010, pp. 72-83.

(Continued)

*Primary Examiner* — Kara E Geisel
*Assistant Examiner* — Maurice Smith
(74) *Attorney, Agent, or Firm* — Ostrager Chong Flaherty & Broitman P.C.

(57) ABSTRACT

A fuel sensing system utilizes a fiber optic sensor comprising a membrane made of a direct band gap semiconductor material (such as gallium arsenide) that forms an optical cavity with an optical fiber inside a hermetically sealed sensor package located at the bottom of a fuel tank. The optical fiber inside the fuel tank is not exposed to the fuel. The optical cavity formed by the bottom surface of the membrane and the surface of the distal end of the internal optical fiber is capable of behaving as a Fabry-Pérot interferometer. Multiple light sources operating at different wavelengths and multiple spectrometers can be coupled to the confronting surface of the membrane via the optical fiber inside the fuel tank, a hermetically sealed fiber optic connector that passes through the wall of the fuel tank, and a fiber optic coupler located outside the fuel tank.

19 Claims, 6 Drawing Sheets

(51) Int. Cl.
*G01F 23/16* (2006.01)
*G01K 1/00* (2006.01)
*G01N 9/00* (2006.01)
*G01N 33/00* (2006.01)
*G01K 11/32* (2006.01)
*G01N 21/65* (2006.01)

(56) References Cited

U.S. PATENT DOCUMENTS

| | | | |
|---|---|---|---|
| 5,072,617 A | 12/1991 | Weiss | |
| 5,763,769 A * | 6/1998 | Kluzner | G01L 23/221 73/114.09 |
| 6,125,218 A | 3/2000 | Humphrey | |
| 6,543,294 B2 * | 4/2003 | Stamps | F16F 9/3264 73/709 |
| 6,687,643 B1 * | 2/2004 | Cason, Jr. | G01F 23/164 361/283.4 |
| 6,775,986 B2 * | 8/2004 | Ganz | F01D 17/085 60/39.281 |
| 7,385,692 B1 | 6/2008 | Nguyen | |
| 2002/0050170 A1 * | 5/2002 | Petrovic | G01L 19/0069 73/715 |
| 2003/0142301 A1 * | 7/2003 | Coleman | G01N 21/65 356/301 |
| 2005/0041905 A1 * | 2/2005 | Lagakos | G01L 7/086 385/12 |
| 2007/0129902 A1 * | 6/2007 | Orbell | B64D 37/02 702/55 |
| 2007/0165238 A1 * | 7/2007 | Boyd | G01L 1/242 356/478 |
| 2007/0187552 A1 * | 8/2007 | Tichborne | B64D 37/02 244/135 R |
| 2007/0272026 A1 * | 11/2007 | Toy | G01L 9/0079 73/724 |
| 2008/0075404 A1 * | 3/2008 | Chin | G01H 9/004 385/12 |
| 2013/0083314 A1 * | 4/2013 | Lambourne | G01D 5/266 356/72 |
| 2013/0100439 A1 * | 4/2013 | Yu | G01N 21/255 356/73 |
| 2013/0206760 A1 * | 8/2013 | Susko | G01D 11/245 220/88.3 |

OTHER PUBLICATIONS

Khotiaintsev et al., "Novel Fiber-Optical Refractometric Sensor Employing Hemispherically-Shaped Detection Element", Optical Engineering, vol. 41, No. 4 (2002).
Zhao et al., "Novel light-leaking optical fiber liquid level sensor for aircraft fuel gauging", Optical Engineering, vol. 52, No. 1 (2013).

* cited by examiner

MULTI-FUNCTIONAL FIBER OPTIC FUEL SENSOR SYSTEM HAVING A PHOTONIC MEMBRANE

BACKGROUND

This disclosure generally relates to systems and methods for measuring a level of liquid in a reservoir, such as a storage tank or other container. More particularly, this disclosure relates to systems and methods for liquid level measurement using an optical sensor.

A need to continuously measure the level of a liquid exists in many commercial and military applications. For example, liquid-level sensors are commonly used in the fuel tanks of aircraft, automobiles and trucks. Liquid-level sensors are also used to monitor liquid levels within storage tanks used for fuel dispensing, wastewater treatment, chemical storage, food processing, etc.

Many transducers for measuring liquid level employ electricity. The electrical output of such transducers changes in response to a change in the liquid level being measured, and is typically in the form of a change in resistance, capacitance, current flow, magnetic field, frequency and so on. These types of transducers may include variable capacitors or resistors, optical components, Hall Effect sensors, strain gauges, ultrasonic devices and so on.

Currently most fuel sensors on aircraft use electricity. For example, existing electrical capacitance sensors require electrical wiring inside the tank, which in turn requires complex installations and protection measures to preclude a safety issue under certain electrical fault conditions. This electrical wiring requires careful shielding, bonding and grounding to minimize stray capacitance and further requires periodic maintenance to ensure electrical contact integrity.

For new airplanes with large fuel tanks incorporated in composite wings, the numbers of fuel sensors is large. Using electrical fuel sensors adds more weight to the airplane not only because of the electrical sensor and electrical cable weight, but also because the metal standoffs and harnesses that support the electrical cables and sensors inside the fuel tank add more weight. And more importantly, with large fuel tanks in composite wings, electromagnetic interference (EMI) and lightning can be a challenge for electrical fuel sensors.

Other approaches involve the use of fiber optic fuel sensors which require one or two fiber optic sensing elements to be placed in the fuel. Any change in fuel density causes changes in the index of refraction of the fuel. This in turn causes a change in the intensity of the light transmitted from one fiber optic sensing element to the other. The problems afflicting fiber optic fuel sensors can include fuel temperature variation, icing in the fuel, and fungus and fuel residue deposit on the fiber optic sensing elements that blocks the light transmission and renders the sensor useless over the lifetime of a commercial airplane.

Other, more complicated, optical methods have been studied. One such method connects fiber optics to a capacitance sensor and converts light to electricity to operate the capacitance sensor and then converts it back to light coming out of the sensor so there are still active electronics within the fuel tank. Some have proposed the use of light-leaking fiber for fuel level measurement but these all employ the principle of refraction and require the fiber to be in contact with the fuel to modulate the light transmission angle at the cladding layer due to the different refractive index of the fuel.

There is room for improvements in systems and methods for sensing properties (such as level, density, temperature and chemical composition) of liquid fuel in a fuel tank.

SUMMARY

The subject matter disclosed herein is directed in part to the design of fiber optic fuel sensor systems that eliminate complex electrical wirings inside fuel tanks for measuring fuel temperature, fuel density, fuel level and fuel chemical composition, while maintaining accuracy and reducing cost, weight and volume as compared to existing electrical sensors. The fiber optic fuel sensor systems disclosed in detail below incorporate fuel sensors which do not need to be in contact with the fuel.

In accordance with one embodiment, the fuel sensing system utilizes a fiber optic sensor comprising a membrane made of a direct band gap semiconductor material (such as gallium arsenide) that forms an optical cavity with an optical fiber inside a hermetically sealed sensor package located at the bottom of the fuel tank. The optical fiber inside the fuel tank is not exposed to (i.e., not in contact with) the fuel. The optical cavity formed by the bottom surface of the membrane and the surface of the distal end of the internal optical fiber is capable of behaving as a Fabry-Pérot interferometer. Multiple light sources operating at different wavelengths and multiple spectrometers can be coupled to the confronting surface of the membrane via the optical fiber inside the fuel tank, a hermetically sealed fiber optic connector that passes through the wall of the fuel tank, and a fiber optic coupler located outside the fuel tank.

For the purpose of illustration, a fuel sensing system that has a membrane made of gallium arsenide (GaAs) will be described in detail below. However, other direct band gap semiconductor materials can be used, such as indium phosphide (InP).

In an embodiment that has a GaAs membrane, the temperature of the fuel can be continuously measured as a function of the reflectivity of the GaAs membrane when light from an 850-nm laser source impinges on the bottom surface of the membrane. The fuel density can be derived from the measured temperature. With fuel density derived, the fuel pressure being exerted on the top surface of the GaAs membrane can be derived from the Fabry-Pérot resonator cavity reflection spectrum of the GaAs membrane using an input broadband source preferably having a wavelength of about 1550 nm. Using the fuel density and fuel pressure, the fuel level of the tank can be measured at any time, i.e., during flight, before flight, and after flight of the airplane. Furthermore, when light from a 1060-nm laser source impinges onto the GaAs membrane, a Raman spectrometer can be used to analyze the optical scattering signal from the fuel, enabling the fuel chemical composition to be monitored continuously.

The system disclosed herein avoids the problems associated with use of electrical sensors because the fiber optic sensor has no electrical wiring inside the fuel tank, and because the optical fiber is in a hermetic package which is not exposed to the fuel, thereby eliminating light blockage due to fuel residue, fungus, fuel dirt deposit and contamination. The fiber optic sensor disclosed herein performs multiple sensing functions, which reduces the weight, size, power and cost of the system, because the number of sensors required for the fuel sensing function is reduced, This multi-functional fiber optic sensor also eliminates the lightning and EMI problems because no electrical wiring or electrical power is required to apply to the sensor placed inside the fuel tank.

One aspect of the subject matter disclosed in detail below is a system for storing a liquid, comprising: a reservoir comprising an enclosure; a chamber-defining structure disposed inside the enclosure that divides an internal volume of the enclosure into a storage compartment and a chamber which are hermetically sealed from each other, the chamber-defining structure comprising a membrane having a top surface that partly defines the storage compartment and a bottom surface that partly defines the chamber, and a housing that supports the membrane and partly defines the chamber; and an optical fiber having a length disposed inside the chamber, the length of optical fiber having a distal end with a surface that confronts the bottom surface of the membrane with a gap therebetween, wherein the membrane is made of a semiconductor material that has a direct band gap. Preferably, membrane is sufficiently thin that the membrane is capable of flexing upward or downward when a magnitude of a pressure being exerted on its top surface changes. In preferred embodiments, the membrane has a thickness in a range of 0.01 mm to 0.5 mm, while the semiconductor material is gallium arsenide or indium phosphide. In one embodiment, the gap has a dimension such that the bottom surface of the membrane and a confronting surface of the distal end of the optical fiber form a Fabry-Pérot resonator cavity. The disclosed system has multiple applications. For example, the reservoir may be incorporated in a wing of an aircraft.

The system described in the preceding paragraph may further comprise: an optical source for outputting light; a spectrometer for converting received light into an electrical signal representing a characteristic of the received light; an optical coupler which optically couples the optical source and the spectrometer to the optical fiber; and a computer system programmed to compute a value of a parameter of liquid contained in the reservoir based on electrical signals received from the spectrometer. The parameter may be selected from the following group: a temperature of the liquid, a pressure of the liquid, a level of the liquid, and a chemical composition of the liquid.

Another aspect of the disclosed subject matter is a system for storing a liquid, comprising: a storage tank; a hermetically sealed package disposed inside the storage tank; the hermetically sealed package comprising a membrane and a length of optical fiber, wherein the membrane has a top surface that is part of an exterior surface of the hermetically sealed package and a bottom surface that is part of an interior surface of the hermetically sealed package, wherein the membrane is made of a semiconductor material that has a direct band gap, and the length of optical fiber has a distal end with a surface that confronts the bottom surface of the membrane with a gap therebetween; a first optical source for outputting light; a first spectrometer for converting received light into an electrical signal representing a characteristic of the received light; and an optical fiber network which optically couples the optical source and the spectrometer to the length of optical fiber, the optical fiber network comprising an optical coupler. In some embodiments, the first optical source is a laser source, the first spectrometer is a temperature probing spectrometer, and the system further comprises a computer system programmed to determine a temperature of liquid contained in the storage tank based on electrical signals received from the temperature probing spectrometer following output of light from the laser source. In other embodiments, the first optical source is a broadband light source, the first spectrometer is a pressure sensing spectrometer, and the system further comprises a computer system programmed to determine a pressure of liquid contained in the storage tank based on electrical signals received from the pressure sensing spectrometer following output of light from the broadband light source. In yet other embodiments, the first optical source is a laser source, the first spectrometer is a Raman spectrometer, and the system further comprises a computer system programmed to determine a chemical composition of liquid contained in the storage tank based on electrical signals received from the Raman spectrometer following output of light from the laser source. In accordance with further embodiments, the system further comprises: a second optical source for outputting light, the second optical source being optically coupled to the length of optical fiber by the optical fiber network; a second spectrometer for converting received light into an electrical signal representing a characteristic of the received light, the second spectrometer being optically coupled to the length of optical fiber by the optical fiber network; and a computer system programmed to compute a level of the liquid contained in the reservoir based on electrical signals received from the first and second spectrometers. In accordance with one embodiment, the first optical source is a laser source, the second optical source is a broadband source, and the computer system is programmed to perform the following operations: determine a temperature of the liquid contained in the storage tank based on electrical signals received from the first spectrometer; calculate a density of the liquid contained in the storage tank based on the determined temperature; determine a pressure of the liquid contained in the storage tank based on electrical signals received from the second spectrometer; and calculate a level of the liquid contained in the storage tank based on the calculated density and the determined pressure.

In accordance with a further aspect, a method for determining a characteristic of liquid stored in a storage tank is provided which comprises: placing a hermetically sealed package inside the storage tank, the hermetically sealed package comprising a membrane and a length of optical fiber, wherein the membrane has a top surface that is part of an exterior surface of the hermetically sealed package and a bottom surface that is part of an interior surface of the hermetically sealed package, wherein the membrane is made of a semiconductor material that has a direct band gap, and the length of optical fiber has a distal end with a surface that confronts the bottom surface of the membrane with a gap therebetween; emitting light from a first optical source that enters a proximal end of the optical fiber, exits the distal end of the optical fiber, and impinges on the bottom surface of the membrane; guiding light from the membrane that enters the distal end of the optical fiber toward a proximal end of the optical fiber after the light has been emitted by the first optical source; measuring a first property of the light that exited the proximal end of the optical fiber using a first spectrometer after the light has been emitted by the first optical source; and processing electronic data output by the first spectrometer to determine a first characteristic of liquid disposed inside the storage tank and on top of the membrane. The foregoing method may further comprise: emitting light from a second optical source that enters a proximal end of the optical fiber, exits the distal end of the optical fiber, and impinges on the bottom surface of the membrane; guiding light from the membrane that enters the distal end of the optical fiber toward a proximal end of the optical fiber after the light has been emitted by the second optical source; measuring a second property of the light that exited the proximal end of the optical fiber using a second spectrometer after the light has been emitted by the second optical source; and processing electronic data output by the second spectrometer to determine a second characteristic of liquid disposed inside the storage tank and on top of the membrane. In one embodiment, the first characteristic is temperature, the second characteristic is pressure, and the method further comprises: calculating a density of the liquid contained in the storage tank based on the determined temperature; and calculating a level of the liquid contained in the storage tank based on the calculated density and the determined pressure.

Other aspects of optical sensor systems suitable for use with liquid storage tanks are disclosed and claimed below.

BRIEF DESCRIPTION OF THE DRAWINGS

Reference will hereinafter be made to the drawings in which similar elements in different drawings bear the same reference numerals.

DETAILED DESCRIPTION

Various embodiments of systems and methods for measurement of a level and other properties of liquid in a reservoir will now be described in detail for the purpose of illustration. At least some of the details disclosed below relate to optional features or aspects, which in some applications may be omitted without departing from the scope of the claims appended hereto.

The basic fuel quality sensor requirements for a fuel tank incorporated in composite wings of an aircraft are fuel temperature, fuel density and fuel level sensing. The sensing function of the sensor needs to be dynamic, which means the sensor should be able to provide these key fuel quality values on the ground or during flight, at different flight envelopes and in extreme temperature and environmental conditions. The multi-function fiber optic sensor disclosed herein is designed to meet the fuel quality sensing requirements for composite wings. The proposed fiber optic sensor eliminates the use of electrical cables and electrical power inside the fuel tank, and eliminates EMI and lightning problems for the composite fuel tank. Furthermore, it reduces the size, weight and power of the electrical sensors used in current commercial airplanes. However, the technology disclosed herein may be applied to other types of liquid reservoirs and is not limited to use in fuel tanks onboard aircraft.

Figure 1:
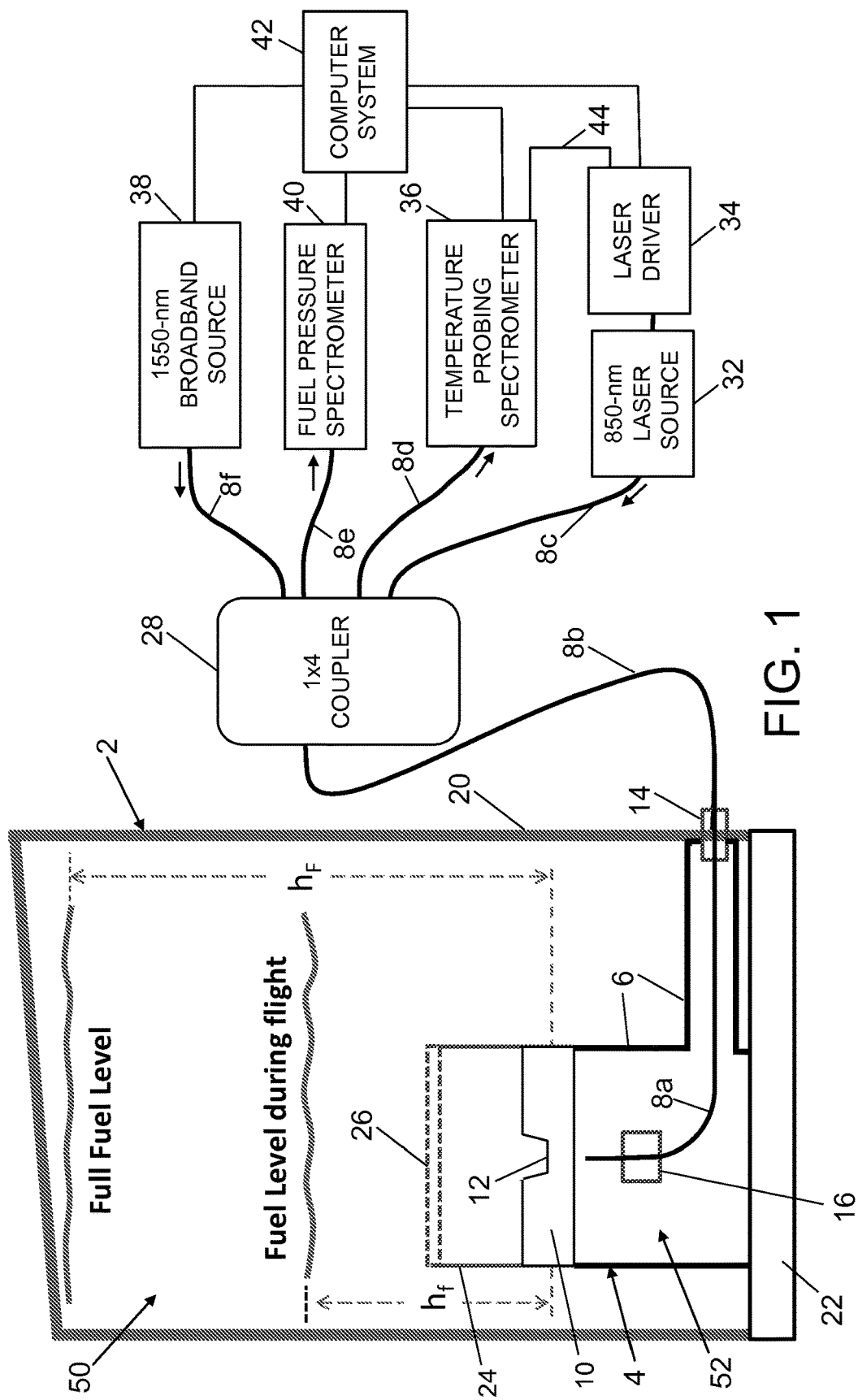
FIG. 1 is a diagram representing components of a multi-function fiber optic fuel sensor system in accordance with one embodiment that uses a GaAs photonic membrane to measure fuel temperature, fuel density and fuel level.

FIG. 1 is a diagram representing components of a multi-function fiber optic fuel sensor system in accordance with one embodiment. The fiber optic fuel sensor of this system can be installed inside a fuel tank 2 comprising a wall 20 and a bottom 22. This fiber optic fuel sensor system uses a GaAs photonic membrane 12 to measure the temperature, density and level of liquid fuel in the fuel tank 2. The thin GaAs membrane 12 is formed in a central portion of a GaAs substrate 10. Gallium arsenide is used instead of silicon because of its superior property for use in temperature sensing. The portion of substrate 10 which surrounds the membrane 12 has a thickness greater than the thickness of the membrane 12. Preferably, the GaAs membrane has a thickness in the range of 0.01 to 0.5 mm and a diameter such that it will be sufficiently flexible when a fuel pressure is exerted on a top surface of the membrane. Preferably the GaAs membrane 12 has a generally horizontal orientation.

The GaAs substrate 10 is a component of a hermetically sealed fiber optic package 4 which can be installed in the fuel tank 2 as a pre-assembled unit. The periphery of the GaAs substrate 10 is bonded to a housing 6 that is also part of the fiber optic package 4. The housing 6 in conjunction with the GaAs substrate 12 effectively divides the internal volume of the fuel tank 2 into a fuel storage compartment 50 (filled with fuel) and a chamber 52 (having no fuel). The GaAs substrate 12 is hermetically sealed to the housing 6 to prevent entry of fuel from the fuel storage compartment 50 to the chamber 52 through the substrate/housing interface.

Preferably at least the space above the GaAs membrane 12 is enclosed and protected by a fine mesh filter 26 that filters out large-size residue, particles or dirt from the fuel occupying the space above the GaAs membrane 12. In the embodiment shown in FIG. 1, the filter 26 is supported by a support wall 24 which surrounds the space above the GaAs substrate 10. The filter support wall 24 may be attached to the periphery of the GaAs substrate 10 or may be an extension of the housing 6 which surrounds and extends above the elevation of the top surface of the GaAs substrate 10. The filter 26 and filter support wall 24 can be incorporated in the pre-assembled fiber optic package 4 or attached after installation of the fiber optic package 4. The filter 26 is configured to admit liquid fuel into the space above the GaAs membrane 12 and inside the support wall 24, while excluding particulate matter from outside that space.

Still referring to FIG. 1, the fiber optic package 4 further comprises an optical fiber 8a, a fiber optic connector 14, and a fiber alignment and locking pedestal 16. The fiber optic connector 14 is fixedly seated in an opening in the housing 6, but has a portion which projects out of the housing 6 and through an opening in the wall 20 of the fuel tank 2 when the package 4 is installed. The fiber optic connector 14 is hermetically sealed in both the opening in the housing 6 and the opening in the wall 20 of the fuel tank 2 so that fuel cannot flow from the fuel storage compartment 50 into the chamber 52 or out of the fuel tank 2 in the area of the fiber optic connector 14.

The fiber alignment and locking pedestal 16 is connected to the bottom of the housing 6 by a support structure not shown in FIG. 1. This support structure may comprise a sufficiently stiff structure which connects the fiber alignment and locking pedestal 16 to a bottom of the housing 6. The connecting structure should be sufficiently rigid that the fiber alignment and locking pedestal 16 is stable and moves as little as possible during operation of the aircraft. More specifically, the fiber alignment and locking pedestal 16 supports the distal end of the optical fiber 8a in a manner such that a surface of that distal end confronts a bottom surface of the GaAs membrane 12 with a small gap of constant length therebetween. That small gap is referred to herein as the optical cavity and is indicated by the label "OC" in FIG. 2 and other figures.

The installation or removal of a pre-assembled unit has the advantage that the entire unit can be readily replaced or removed for repair in the event of a malfunction. However, in alternative embodiments the optical fiber 8a and GaAs substrate 10 could be supported in the same spatial relationship using a support structure which is integrated with the fuel tank 2 so long as the support structure defines a hermetically sealed chamber in which the optical fiber is not in contact with the fuel in the fuel tank.

In the embodiment depicted in FIG. 1, the membrane is made of gallium arsenide, which is a direct band gap material. However, other direct band gap materials can be used, such as indium phosphide (InP). A band gap is "direct" if the momentum of electrons and holes is the same in both the conduction band and the valence band, meaning that an electron can directly emit a photon without passing through an intermediate state and transferring momentum to the crystal structure.

The optical fiber 8a (preferably multi-mode, but single-mode is acceptable) inside the hermetically sealed fiber optical package 4 is aligned with and confronts the bottom surface of the GaAs membrane 12 in the central portion of the GaAs substrate 10. The term single-mode is meant to include optical fibers with core diameter range from 8 to 10 microns which transmit only a single optical waveguide mode in the fiber. Single-mode fibers are glass optical fibers with total diameter about 125 microns with the cladding around the core. Similarly, the term multi-mode is meant to include optical fibers with core diameters from 50 microns to 1 mm. Multi-mode fibers transmit multiple optical waveguide modes in the fiber because of their large core diameter. Multi-mode fibers can be made of glass or plastic. Glass multi-mode optical fibers have total diameters in a range from 125 to 140 microns with the cladding around the core, while plastic multi-mode fibers have core diameters in a range from 0.1 to 0.98 mm and total diameters in a range from 0.25 to 1 mm with the cladding around the core. Preferably the distal end of the optical fiber 8a is aligned precisely with a center of the GaAs membrane 12 and attached to the fiber alignment and locking pedestal 16 using a high-reliability fiber soldering process. The proximal end of the optical fiber 8a is optically coupled to one end of an optical fiber 8b (disposed outside the fuel tank 2) by the hermetic and leakproof fiber optic connector 14 inserted in an opening in the wall 20 of the fuel tank 2.

The optical fiber 8a inside the fuel tank 2 is optically coupled to the output side of a 1×4 fiber optic coupler 28 by the optical fiber 8b. The function of the 1×4 fiber optic coupler 28 is to couple the optical signal from an optical source located outside the fuel tank 2 into the optical fiber 8a inside the fuel tank 2 and then couple the optical signal from the optical fiber 8a into a spectrometer located outside the fuel tank 2 for analysis of the optical signal coming from the GaAs membrane 12. On the other side, the 1×4 fiber optic coupler 28 is connected to four optical fibers 8c through 8f.

One pair of optical fibers 8c and 8d are used for heating and temperature sensing of the bottom surface of the GaAs membrane 12. The optical fiber 8c is connected to a laser source 32 (e.g., a laser diode) which is driven by a laser driver 34 to provide a 850-nm laser source (by way of fiber optic coupler 28, optical fiber 8b, fiber optic connector 14, and optical fiber 8a) to illuminate the bottom surface of the GaAs membrane 12. The optical fiber 8a inside the fiber optic package 4 couples the 850-nm optical signal to the bottom surface of the GaAs membrane 12 across the optical cavity. The optical signal representing the reflection from the bottom surface of GaAs membrane 12 (indicated by an arrow adjacent to optical fiber 8d in FIG. 1) is coupled by the optical fiber 8a, fiber optic connector 14, optical fiber 8b, fiber optic coupler 28, and optical fiber 8d back to a temperature probing spectrometer 36.

Figure 2:
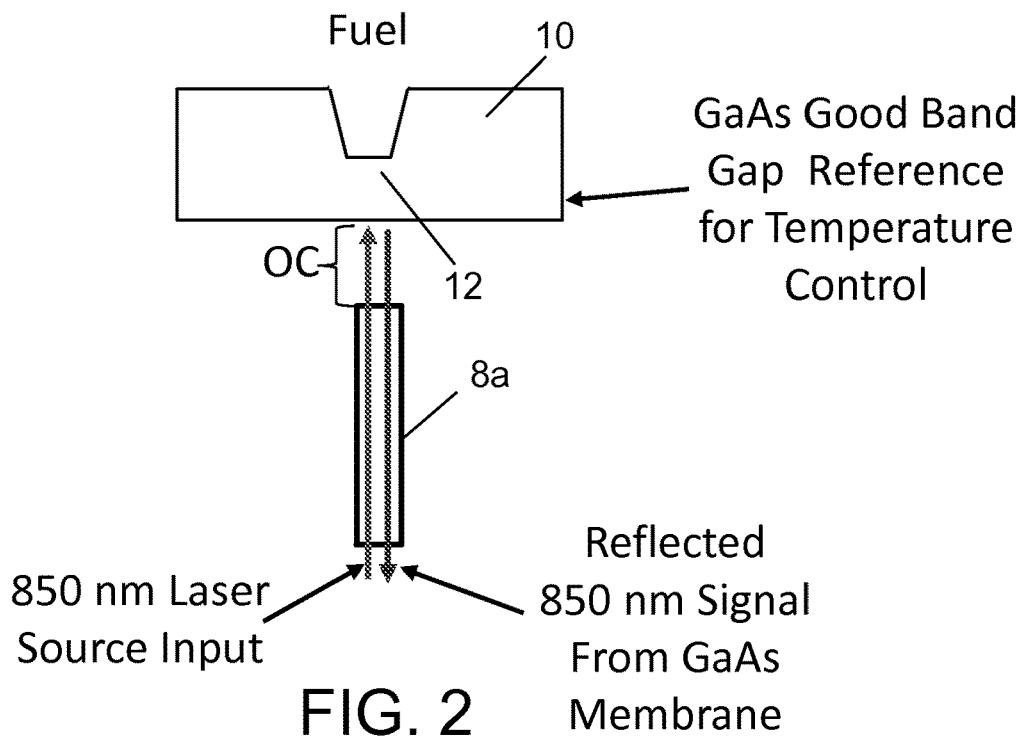
FIG. 2 is a diagram demonstrating the GaAs photonic membrane fuel temperature sensing principle employed by the fiber optic fuel sensor system schematically depicted in FIG. 1.

FIG. 2 is a diagram demonstrating the GaAs photonic membrane fuel temperature sensing principle employed by the fiber optic fuel sensor system schematically depicted in FIG. 1. Gallium arsenide is a semiconductor which has a direct band gap that varies with temperature: as the temperature of the fuel decreases, the GaAs membrane band gap increases. This reduces the absorption of the 850-nm signal (indicated by an upward arrow in FIG. 2). When the absorption is reduced, the reflection signal (indicated by a downward arrow in FIG. 2) increases. As the fuel temperature increases, the band gap of the GaAs membrane 12 decreases. This decrease in band gap has the effect of increasing the absorption the 850-nm light signal and reducing the reflection of the 850-nm signal. The increase and decrease in the amount of reflected light is precisely detected and analyzed by the temperature probing spectrometer 36.

Figure 3:
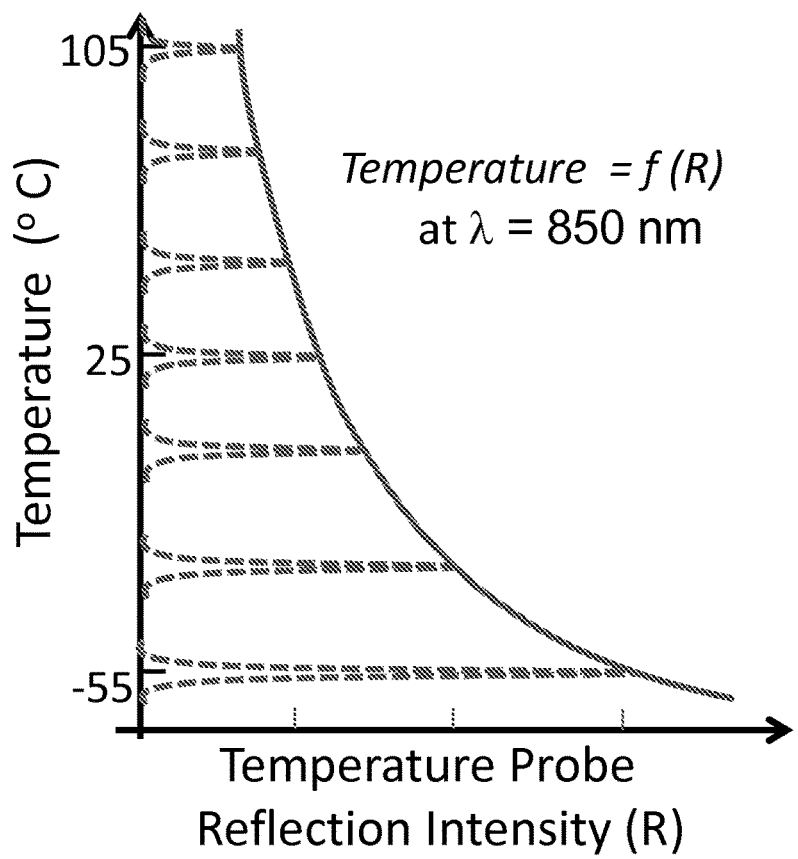
FIG. 3 is a graph of GaAs photonic membrane temperature (in ° C.) versus reflection intensity R for impinging light having a wavelength of 850 nm.
Figure 4:
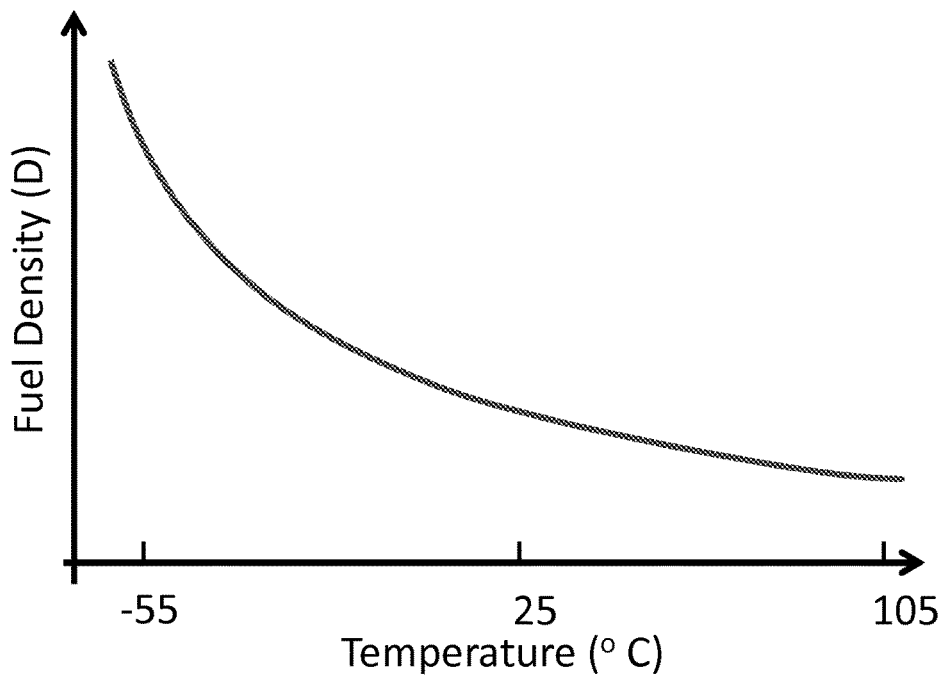
FIG. 4 is a graph of fuel density D versus fuel temperature (in ° C.).

FIG. 3 is a graph of GaAs photonic membrane temperature (in ° C.) versus reflection intensity R for 850-nm coherent light impinging on a GaAs membrane. Based on the data represented by the curve shown in FIG. 3, the temperature probing spectrometer 36 measures the temperature of the fuel instantaneously and outputs electrical signals representing that fuel temperature to a computer system 42. Since the fuel density is a well-known function of temperature as shown in FIG. 4, the computer system 42 can process the fuel temperature information and perform the necessary calculations for determining the fuel density D instantaneously. Using the temperature measured by the temperature probing spectrometer 36, the density of the fuel can be determined by the computer system 42 any time during flight or while the aircraft is on the ground.

After the fuel density D has been determined, the fuel level can be determined from the fuel pressure measured at the GaAs membrane 12. Returning to FIG. 1, the other pair of optical fibers 8e and 8f are used for sensing the fuel pressure being exerted on the GaAs membrane 12. The optical fiber 8f is connected to a broadband light source 38 which is driven to provide a spectrum of light centered at 1550 nm with a flat spectral width of about 40 nm (by way of fiber optic coupler 28, optical fiber 8b, fiber optic connector 14, and optical fiber 8a) to illuminate the bottom surface of the GaAs membrane 12. The optical fiber 8a inside the fiber optic package 4 couples the 1550-nm optical signal to the bottom surface of the GaAs membrane 12 across the optical cavity. The optical signal representing the reflections of the broadband light from the bottom surface of GaAs membrane 12 (indicated by an arrow adjacent to optical fiber 8e in FIG. 1) is coupled by the optical fiber 8a, fiber optic connector 14, optical fiber 8b, fiber optic coupler 28, and optical fiber 8e back to a pressure sensing spectrometer 40.

Figure 5:
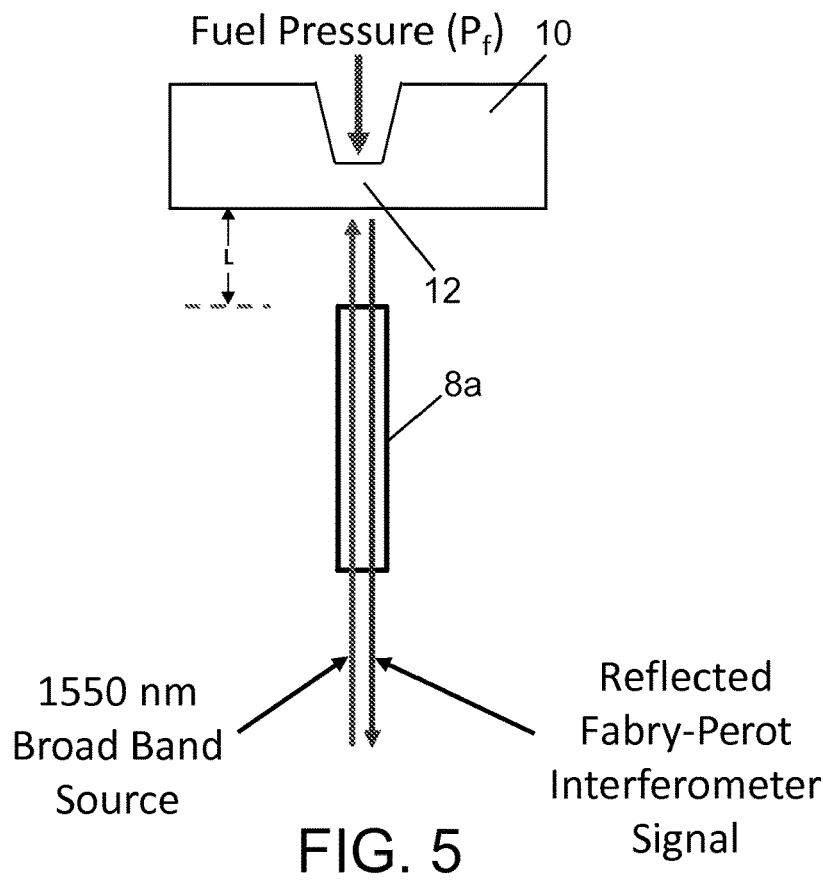
FIG. 5 is a diagram demonstrating the GaAs photonic membrane fuel pressure sensing principle employed by the fiber optic fuel sensor system schematically depicted in FIG. 1.

FIG. 5 is a diagram demonstrating the GaAs photonic membrane fuel pressure sensing principle employed by the fiber optic fuel sensor system schematically depicted in FIG. 1. The distance separating the surface of the distal end of the optical fiber 8a and the confronting portion of the bottom surface of the GaAs membrane 12 (referred to herein as the "optical cavity length") is indicated by a variable length L in FIG. 1. When the fuel compartment 50 (see FIG. 1) is empty, the optical cavity length has a value $L_0$; in contrast, when the fuel compartment 50 has sufficient fuel that the space above the GaAs membrane 12 is at least partially occupied by fuel, then that fuel will exert a downward pressure on the flexible GaAs membrane 12. The fuel pressure exerted on the GaAs membrane 12 causes a downward deflection of the membrane 12, thereby reducing the optical cavity length L. Since the bottom surface of the GaAs membrane 12 and the surface of the distal end of the optical fiber 8a form a Fabry-Pérot resonator cavity (a.k.a. a Fabry-Pérot interferometer), the change in the optical cavity length ΔL can be measured by the pressure sensing spectrometer 40 using the multiple reflections returned by from Fabry-Pérot resonator cavity.

As shown in FIG. 1, the fuel level height is dynamically changing. Upon fuel fill-up on the ground, the full (i.e., initial) fuel level is $h_F$. In contrast, during flight the in-flight (i.e., current) fuel level is $h_f$. More specifically, $h_F$ is the height measured from the elevation of the GaAs membrane 12 to the full level of fuel in the fuel tank, while $h_f$ is the height measured from the elevation of the GaAs membrane 12 to the current level of fuel in the fuel tank 2 The relationships between the respective pressures $P_F$ and $P_f$ (at fill-up and in flight, respectively) exerted on the GaAs membrane, the fuel density D, and the fuel levels $h_F$ and $h_f$ can be described by the following equations:

$$P_F = \frac{F}{A} = \frac{mg}{A} = \frac{DV_F g}{A} = \frac{Dh_F A g}{A} = Dh_F g \quad (1)$$

$$h_F = \frac{Dg}{P_F} \quad (2)$$

$$P_f = Dh_f g \quad (3)$$

$$h_f = \frac{Dg}{P_f} \quad (4)$$

In Eqs. (1) through (4), m is the mass of fuel, g is gravitational acceleration, A is the GaAs membrane pressure sensing area, and $V_F$ is the volume of fuel overlying the area A upon fill-up. The relationship of the full fuel level height $h_F$ to fuel density D is given in Eq. (2); the relationship of the in-flight fuel level $h_f$ to fuel density D is given in Eq. (4). Since density D can be determined by the computer system 42 based on the measurement data from the temperature probing spectrometer 36, the fuel levels $h_F$ and $h_f$ can be determined after the respective pressures $P_F$ and $P_f$ have been measured by the pressure sensing spectrometer 40.

In FIG. 5, the optical cavity length L formed by the bottom surface of the GaAs membrane 12 and the confronting surface of the distal end of the optical fiber 8a is given by the following equation:

$$L = \frac{\lambda_i^2}{2n_{eff} \times \Delta\lambda} \quad (5)$$

where $\lambda_i$ is the operating wavelength (e.g., 1550 nm), Δλ is the free spectral range of the optical cavity, and $n_{eff}$ is the index of refraction for air.

Figure 6:
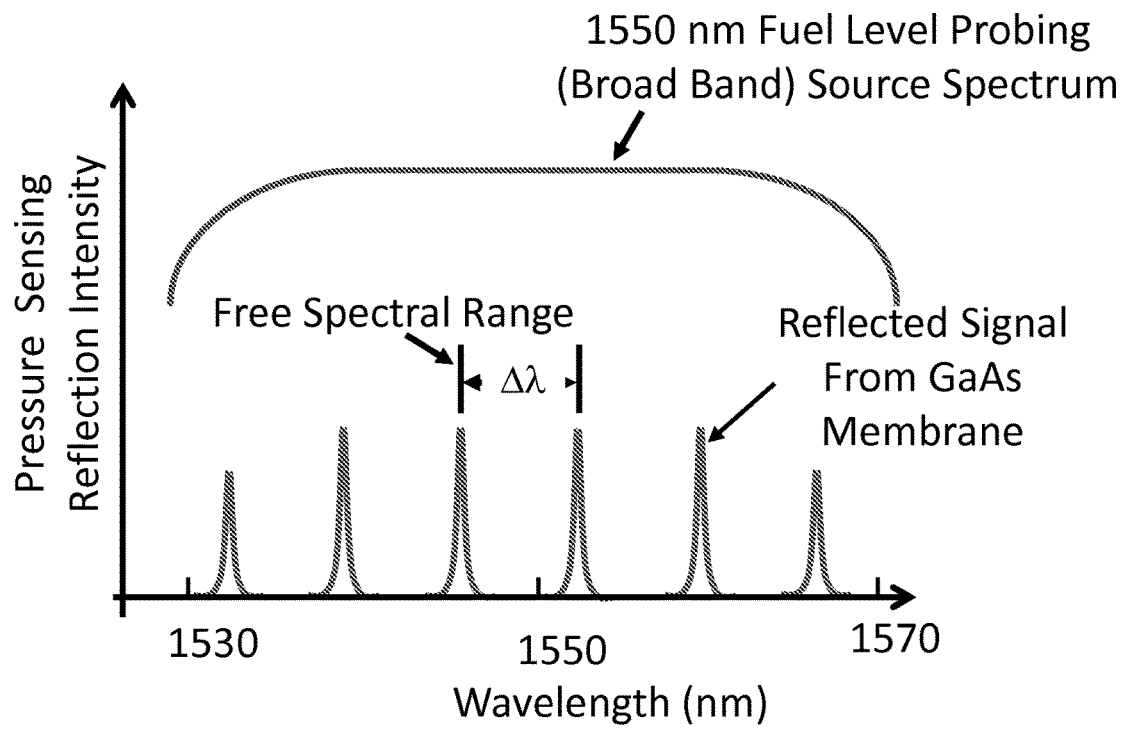
FIG. 6 is a graph showing the pressure sensing reflection intensity over a range of wavelengths for light signals reflected from the GaAs photonic membrane to a pressure sensing spectrometer incorporated in the fiber optic fuel sensor system schematically depicted in FIG. 1.

Using Eq. (5), L can be determined from the measurement of the free spectral range Δλ. FIG. 6 is a graph showing the pressure sensing reflection intensity over a range of wavelengths for light signals reflected from the GaAs photonic membrane 12 to the pressure sensing spectrometer 40. As seen in FIG. 6, Δλ can be measured by pumping a 1550-nm broadband spectrum of light into the optical fiber 8a and then acquiring optical signals reflected from the GaAs membrane 12 back into the optical fiber 8. The pressure-sensing spectrometer 40 then determines the spacing between the reflected signal peaks of respective wavelengths within the bandwidth of the broadband source. This peak wavelength spacing corresponds to the free spectral range Δλ.

The upper curve in FIG. 6 represents the spectrum of the broadband source centered at 1550 nm with a flat spectral width of about 40 nm. The reflected signal spectrum from the GaAs membrane is shown in the lower part of FIG. 6. The peaks in this spectrum are the resonant peaks of the Fabry-Pérot resonator cavity (OC in FIG. 6) formed between the surface of the distal end of the optical fiber 8a and the confronting bottom surface of the GaAs membrane 12. The spacing between these periodic resonant peaks is the free spectral range Δλ. As the fuel level change, the free spectral range is instantaneously measured by the pressure sensing spectrometer 40 (see FIG. 1). This information is output to the computer system 42, which performs computations to determine the fuel level After the optical cavity length L has been measured, the current fuel pressure $P_f$ can be derived from L using the following equations, which apply the mechanical theory of membranes:

$$\Delta L = 0.318 l^3 \sqrt{\frac{P_f l}{Eh}} \quad (6)$$

$$P_f = \frac{Eh(\Delta L)^3}{0.0322 l^4} \quad (7)$$

where ΔL is change in the optical cavity length due to the displacement or deflection of the GaAs membrane 12, l is the membrane width, h is the membrane thickness, and E is Young's modulus. As previously noted, $\Delta L = L_0 - L$, where $L_0$ is the optical cavity length when the fuel compartment 50 is empty, and L is derived from Eq. (5).

The fuel pressure $P_f$ derived from Eq. (7) can be used in Eq. (4) to derive the height $h_f$ from the elevation of the GaAs membrane 12 to the current level of fuel in the fuel tank 2. The fuel pressure $P_F$ can be derived in a similar manner and used in Eq. (2) to derive the height $h_F$ from the deflection of the GaAs membrane 12 to the full fuel level.

Referring again to FIG. 1, the computer system 42 is programmed to perform the calculations previously described and is further programmed to control the light sources and the spectrometers. In particular, the computer system 42 is programmed to monitor the operation of the 850-nm laser source 32 and the 1550-nm broadband source 38; it also controls the test and measurement function of the temperature probing spectrometer 36 and the fuel pressure sensing spectrometer 40.

The computer system 42 monitors the 850-nm laser source 32 and the laser driver 34 to provide an automatic temperature control loop 44 to drive the 850-nm laser source 32 for constant light output power over the airplane's operating temperature range and other extreme environmental conditions. For example, the computer system 42 can be programmed to increase the power of the 850-nm laser source 32 to melt any ice formed on the exterior surface of the GaAs membrane 12. This capability can also be used to clean the exterior surface of the GaAs membrane 12 by slightly heating the membrane with higher 850-nm laser power within the allowable heating limit of the fuel tank 2.

Figure 7:
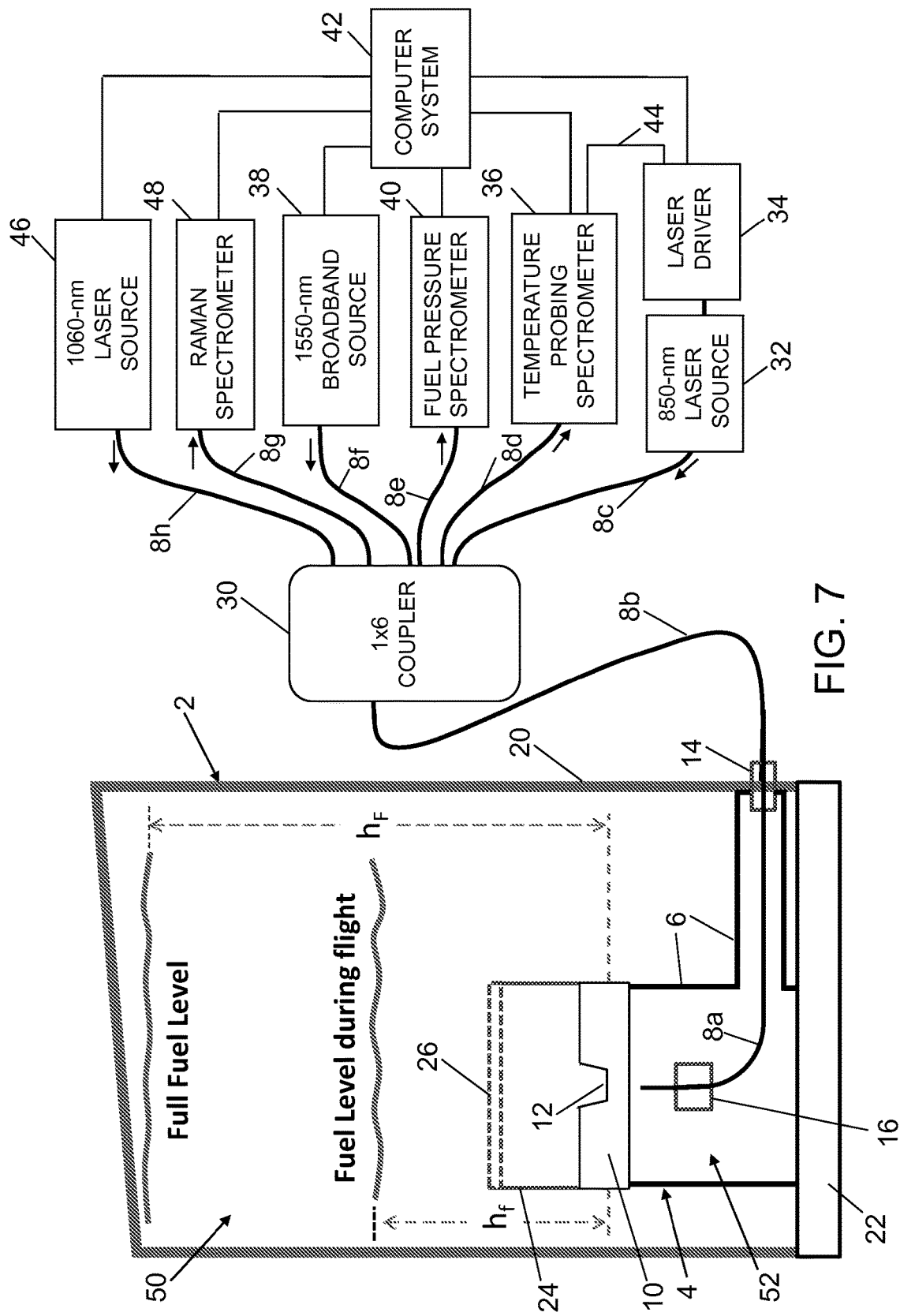
FIG. 7 is a diagram representing components of a multi-function fiber optic fuel sensor system in accordance with one embodiment that uses a GaAs photonic membrane to measure fuel temperature, fuel density, fuel level and fuel chemical composition.

For more advanced fuel quality monitoring, the sensor system depicted in FIG. 1 can be enhanced by adding components which monitor the fuel's chemical composition. This enhancement is shown in FIG. 7. The system depicted in FIG. 7 differs from that shown in FIG. 1 in that a 1060-nm laser source 46 and a Raman spectrometer 48 for determining fuel chemical composition are added; the 1×4 fiber optic coupler 28 is replaced by a 1×6 fiber optic coupler 30; and a pair of optical fibers 8g and 8h are added to connect the 1×6 fiber optic coupler 30 to the 1060-nm laser source 46 and the Raman spectrometer 48. These components are used for monitoring the fuel chemical composition in the fuel tank 2 for fuel quality assurance. The optical fiber 8g is connected with the 1060-nm laser source 46 and the optical fiber 8h is connected to the Raman spectrometer 48. The 1060-nm laser source 46 is optically coupled into the optical fiber 8a inside the fuel tank 2 through the 1×6 fiber optic coupler 30. The scattering optical signal from the fuel occupying the space above the GaAs membrane 12 passes through the membrane, enters the distal end of the optical fiber 8a, and is then coupled into the Raman spectrometer 48 through the 1×6 fiber optic coupler 30.

Figure 8:
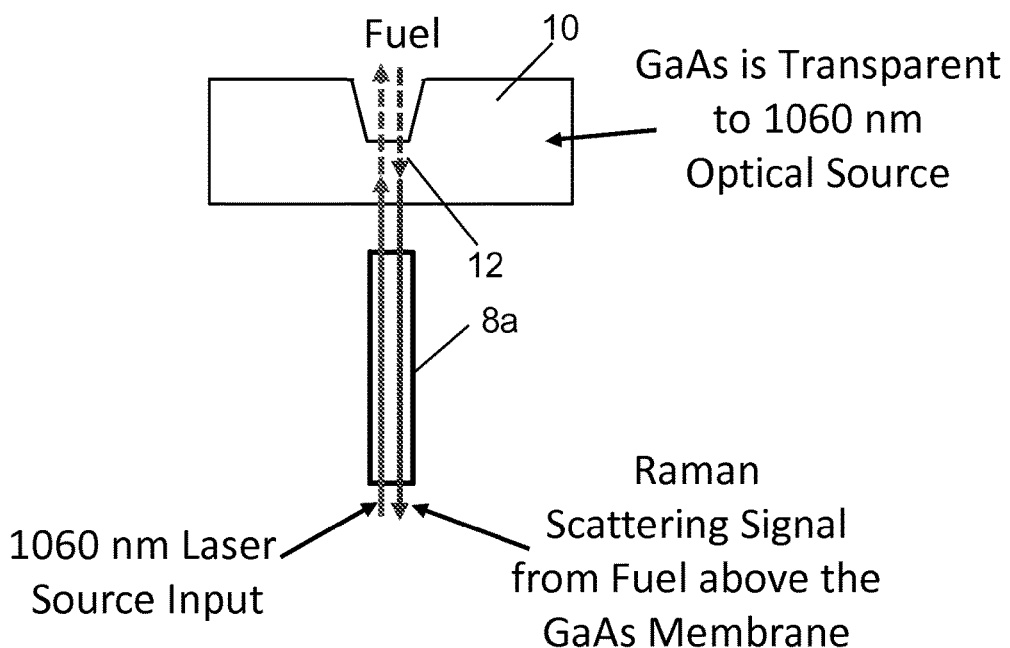
FIG. 8 is a diagram demonstrating the principle underlying the method of sensing the fuel chemical composition employed by the fiber optic fuel sensor system schematically depicted in FIG. 7, which method uses a GaAs photonic membrane and the Raman technique.

FIG. 8 is a diagram demonstrating the principle underlying the method of sensing the fuel chemical composition employed by the fiber optic fuel sensor system schematically depicted in FIG. 7, which method uses a GaAs photonic membrane 12 and the Raman technique. The 1060-nm laser beam that is coupled into the optical fiber 8a is transparent to the GaAs membrane 12 (as indicated by the dashed arrow pointing upward in FIG. 8). This is due to the larger band gap of GaAs as compared to the photon energy of the 1060-nm laser beam. Taking advantage of the GaAs transparency to 1060-nm coherent light, the 1060-nm laser beam passes through the GaAs membrane 12 and into the space above the membrane, which is occupied by the fuel. The 1060-nm photons excite the electrons in the fuel molecules to higher vibration states. As these excited electrons relax to their respective ground states, they emit photons which have less energy than the absorbed photon, producing a shift in wavelength from the 1060-nm source wavelength. This energy difference is the well-known Stokes shift of the material being excited. Different molecules have different Stokes shifts, which property can be used to determine the chemical composition of the fuel. The chemical composition at different times can be compared to indicate changes in the fuel's molecular structure. Monitoring the fuel molecular structure is very important for fuel quality assurance. The Raman scattering signal is coupled through the GaAs membrane 12 back into the optical fiber 8a inside the fuel tank 2 and then to the Raman spectrometer 48 outside the fuel tank 2. The Raman spectrometer 48 then analyzes the spectrum of the light returned from the fuel and outputs a Raman "signature" containing information representing the signal intensity as a function of wave number. The Raman spectrometer 48 outputs those signatures to the computer system 42, which is programmed to compare an incoming Raman signatures to a reference Raman signature, determine the respective shifts in peak wavelengths manifested in the incoming Raman signature, and then identify any changes in fuel chemical composition based on those shifts in peak wavelength.

Figure 9:
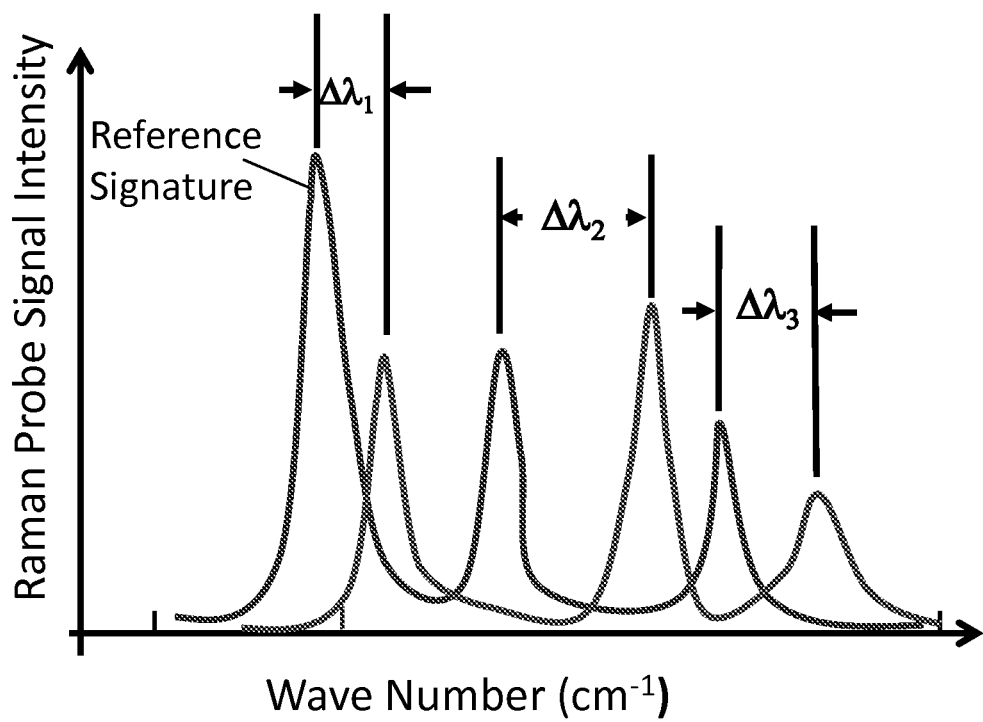
FIG. 9 is a graph showing changes in signal intensity versus wave number detected by a Raman spectrometer, which changes correspondingly to indicate a change in fuel chemical composition.

FIG. 9 is a graph showing shifts in peak signal intensity versus wave number detected by the Raman spectrometer 48. These shifts in peak signal intensities indicate changes in fuel chemical composition. In the example shown in FIG. 9, one Raman signature (indicated as the "Reference Signature" in FIG. 9) represents the Raman spectrum for fuel having an initial chemical composition. The other Raman signature in FIG. 9 represents the Raman spectrum for fuel having a chemical composition which deviates from the initial chemical composition represented by the first Raman signature. Respective shifts in peak wavelengths are indicated by $\Delta\lambda_1$, $\Delta\lambda_2$ and $\Delta\lambda_3$ in FIG. 9. These shifts indicate that a change in fuel chemical composition has occurred.

The computer system 42 monitors the 1060-nm laser source 46 for constant output power over the airplane's operating temperature, and it also monitors the operation of the Raman spectrometer 48 for calibration, detection and measurement.

The optical coupler 28 and optical fibers 8c through 8f depicted in FIG. 1 form an optical network. Similarly, the optical coupler 30 and optical fibers 8c through 8h depicted in FIG. 7 form an optical network The fiber optic sensor disclosed above uses proven and qualified optical fibers, optical components and measurement equipment. No capacitance sensing and measurement are required; the sensor has no active electronic operation inside the fuel tank. No shielding/bonding/grounding of signal wiring is required. There is no possibility of igniting the fuel. The sensor is not afflicted with complications due to stray wiring capacitance/inductance. As a result of using optical fuel sensors to measure fuel levels, the weight and cost of an airplane can be reduced. Also the sensing optical fiber is not exposed or in contact with the fuel.

Each optical fiber is a flexible, optically transparent or translucent fiber made of extruded glass or plastic. It can function as a waveguide or light pipe to transmit light between the two ends of the fiber. Optical fibers typically include a transparent or translucent core having a relatively higher index of refraction surrounded by a transparent or translucent cladding material having a relatively lower index of refraction. Light is kept in the core by total internal reflection. This causes the optical fiber to act as a waveguide.

The computer system 42 may comprise one or more dedicated microprocessors or one or more general-purpose computers, and may calculate the measured level (i.e., height) of the fuel by using a look-up table, a calibration curve, or by solving equations, as appropriate. A fuel gauge (not shown in the drawings) displayed in the cockpit may be controlled to indicate the amount of fuel present within the fuel tank based on the spectrometry data received by the computer system 42.

The computer system 42 may be a computer or part of a flight control system located on an aircraft. In identifying the amount of fuel present in an irregular-shaped fuel tank, the computer system 42 may execute various routines to calculate the amount of fuel present based on data received from multiple GaAs membranes appropriately placed in various compartments of the fuel tank. The fuel information processing software may include routines that take into account the shape of the fuel tank to determine the amount of fuel remaining in the fuel tank. The fuel information processing software may further include routines for calibrating processes to form a baseline before a first use or to maintain accuracy of fuel readings. The readings provided by the computer system 42 to the fuel gauge may be integrated or averaged before presentation and may be provided at different time intervals.

In the example shown in FIGS. 1 and 7, optical fibers are used to measure the level of fuel in a fuel tank. In other embodiments, the same apparatus may be used to detect other liquids. For example, the system described above may be used to detect the presence of water in a container or hydraulic fluids in a reservoir for a hydraulic system. The illustration of detecting fuel in a fuel tank is presented for purposes of illustration and not meant to limit the manner in which the systems shown in FIGS. 1 and 7 may be used.

A wing fuel tank system that uses electrical sensors can be retrofitted by substituting the optical sensors disclosed herein. Double shielded electrical wiring for the electrical sensors can be replaced with light and flexible plastic optical fiber, eliminating weight from the wiring and supporting brackets, and eliminating electromagnetic effects from lightning, shorting, fraying of electrical wiring.

While optical fuel sensors having membranes made of direct band gap semiconductor material have been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit.

In addition, the method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. A system for storing a liquid, comprising:
a reservoir comprising an enclosure;
a chamber-defining structure disposed inside said enclosure that divides an internal volume of said enclosure into a storage compartment and a chamber which are hermetically sealed from each other, said chamber-defining structure comprising a membrane having a top surface that partly defines said storage compartment and a bottom surface that partly defines said chamber, and a housing that supports said membrane and partly defines said chamber, wherein said membrane is made of a semiconductor material that has a direct band gap;
an optical fiber having a length disposed inside said chamber, said length of optical fiber having a distal end with a surface that confronts said bottom surface of said membrane with a gap therebetween,
a broadband light source for outputting broadband light;
a first spectrometer for converting received broadband light into an electrical signal representing a characteristic of the received broadband light;
a coherent light source for outputting coherent light;
a second spectrometer converting received coherent light into an electrical signal representing a characteristic of the received coherent light;
an optical coupler which optically couples said broadband light source, said coherent light source, and said first and second spectrometers to said optical fiber; and
a computer system programmed to compute a value of a pressure of the liquid contained in the reservoir based on electrical signals received from said first spectrometer following the output of broadband light by said broadband light that impinges on and is reflected from said membrane and compute a value of a temperature of the liquid contained in the reservoir based on electrical signals received from said second spectrometer following the output of coherent light by said coherent light source that impinges on and is reflected from said membrane.

2. The system as recited in claim 1, wherein said membrane is sufficiently thin that said membrane is capable of flexing upward or downward when a magnitude of a pressure being exerted on its top surface changes.

3. The system as recited in claim 2, wherein said membrane has a thickness in a range of 0.01 to 0.5 mm.

4. The system as recited in claim 1, wherein said semiconductor material is gallium arsenide or indium phosphide.

5. The system as recited in claim 1, wherein said optical fiber is a single-mode or multi-mode optical fiber.

6. The system as recited in claim 1, further comprising:
a filter support wall that surrounds a space inside said storage compartment that overlies said membrane; and
a filter supported by said filter support wall, said filter being configured to admit liquid into said space while excluding particulate matter from outside said space.

7. The system as recited in claim 1, wherein said gap has a dimension such that said bottom surface of said membrane and a confronting surface of said distal end of said optical fiber form a Fabry-Pérot resonator cavity.

8. The system as recited in claim 1, further comprising a fiber optic connector seated in and hermetically sealed to an opening in said enclosure and to an opening in said housing, wherein another end of said length of said optical fiber is coupled to said fiber optic connector.

9. The system as recited in claim 1, wherein said reservoir is incorporated in a wing of an aircraft.

10. A system for storing a liquid, comprising:
a storage tank;
a hermetically sealed package disposed inside said storage tank; said hermetically sealed package comprising a membrane and a length of optical fiber, wherein said membrane has a top surface that is part of an exterior surface of said hermetically sealed package and a bottom surface that is part of an interior surface of said hermetically sealed package, wherein said membrane is made of a semiconductor material that has a direct band gap, and said length of optical fiber has a distal end with a surface that confronts said bottom surface of said membrane with a gap therebetween;

a laser source for outputting coherent light;

a temperature probing spectrometer for converting received coherent light into an electrical signal representing a characteristic of the received coherent light;

an optical fiber network which optically couples said laser source and said temperature probing spectrometer to said length of optical fiber; and a computer system programmed to determine a temperature of liquid contained in said storage tank based on electrical signals received from said temperature probing spectrometer following output of coherent light from said laser source that impinges on and is reflected from said membrane.

11. The system as recited in claim 10, wherein said semiconductor material is gallium arsenide or indium phosphide.

12. A system for storing a liquid, comprising:

a storage tank;

a hermetically sealed package disposed inside said storage tank; said hermetically sealed package comprising a membrane and a length of optical fiber, wherein said membrane has a top surface that is part of an exterior surface of said hermetically sealed package and a bottom surface that is part of an interior surface of said hermetically sealed package, wherein said membrane is made of a semiconductor material that has a direct band gap, and said length of optical fiber has a distal end with a surface that confronts said bottom surface of said membrane with a gap therebetween;

a first optical source for outputting light;

a first spectrometer for converting received light into an electrical signal representing a characteristic of the received light; and an optical fiber network which optically couples said first optical source and said first spectrometer to said length of optical fiber, said optical fiber network comprising an optical coupler, wherein said first optical source is a laser source that produces coherent light having a wavelength, said membrane is transparent to coherent light of said wavelength, and said first spectrometer is a Raman spectrometer which receives light scattered back though said membrane by liquid contained in said storage tank, further comprising a computer system programmed to determine a chemical composition of liquid contained in said storage tank based on electrical signals received from said Raman spectrometer following output of said coherent light from said laser source.

13. The system as recited in claim 12, further comprising:

a second optical source for outputting light; and a second spectrometer for converting received light into an electrical signal representing a characteristic of the received light, wherein the optical fiber network optically couples said second optical source and said second spectrometer to said length of optical fiber.

14. The system as recited in claim 13, wherein said second optical source is a laser source, said second spectrometer is a temperature probing spectrometer, and said computer system is further programmed to determine a temperature of liquid contained in said storage tank based on electrical signals received from said temperature probing spectrometer following output of light from said second optical source.

15. The system as recited in claim 13, wherein said second optical source is a broadband light source, said second spectrometer is a pressure sensing spectrometer, and said computer system is further programmed to determine a pressure of liquid contained in said storage tank based on electrical signals received from said pressure sensing spectrometer following output of light from said second optical source.

16. The system as recited in claim 12, wherein said semiconductor material is gallium arsenide or indium phosphide.

17. A method for determining a temperature of liquid stored in a storage tank, comprising:

placing a hermetically sealed package inside the storage tank, the hermetically sealed package comprising a membrane and a length of optical fiber, wherein the membrane has a top surface that is part of an exterior surface of the hermetically sealed package and a bottom surface that is part of an interior surface of the hermetically sealed package, wherein the membrane is made of a semiconductor material that has a direct band gap, and the length of optical fiber has a distal end with a surface that confronts the bottom surface of the membrane with a gap therebetween;

emitting coherent light from a laser source that enters a proximal end of the optical fiber, exits the distal end of the optical fiber, and impinges on the bottom surface of the membrane;

guiding coherent light from the membrane that enters the distal end of the optical fiber toward a proximal end of the optical fiber after the coherent light has been emitted by the first optical source;

measuring a first property of the coherent light that exited the proximal end of the optical fiber using a temperature probing spectrometer after the coherent light has been emitted by the laser source; and processing electronic data output by the temperature probing spectrometer to determine a temperature of liquid disposed inside the storage tank and on top of the membrane.

18. The method as recited in claim 17, further comprising:

emitting broadband light from a broadband light source that enters a proximal end of the optical fiber, exits the distal end of the optical fiber, and impinges on the bottom surface of the membrane;

guiding broadband light from the membrane that enters the distal end of the optical fiber toward a proximal end of the optical fiber after the broadband light has been emitted by the second optical source;

measuring a second property of the broadband light that exited the proximal end of the optical fiber using a pressure spectrometer after the broadband light has been emitted by the broadband light source; and processing electronic data output by the pressure spectrometer to determine a pressure of liquid disposed inside the storage tank and on top of the membrane.

19. The method as recited in claim 18, further comprising:

calculating a density of the liquid contained in the storage tank based on the determined temperature; and calculating a level of the liquid contained in the storage tank based on the calculated density and the determined pressure.

* * * * *